US006867350B2

(12) United States Patent
Ferl et al.

(10) Patent No.: US 6,867,350 B2
(45) Date of Patent: Mar. 15, 2005

(54) PLANTS WITH ENHANCED ABILITY TO PRODUCE STARCH AND METHODS FOR OBTAINING THEM

(75) Inventors: Robert J. Ferl, Gainesville, FL (US); Paul C. Sehnke, Gainesville, FL (US); Hwa Jee Chung, Seoul (KR); Ke Wu, Gainesville, FL (US); L. Curtis Hannah, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/859,822

(22) Filed: May 17, 2001

(65) Prior Publication Data

US 2002/0062497 A1 May 23, 2002

Related U.S. Application Data

(60) Provisional application No. 60/204,746, filed on May 17, 2000.

(51) Int. Cl.$^7$ ..................... C12N 15/29; C12N 15/82; A01H 1/00; A01H 5/00; A01H 5/10

(52) U.S. Cl. ..................... 800/284; 800/286; 800/298; 800/306; 800/312; 800/317.2; 800/317.3; 800/320; 800/320.1; 800/320.2; 800/320.3; 435/419; 435/421

(58) Field of Search ..................... 800/278, 284, 800/285, 286, 295, 320, 320.1, 320.2, 320.3, 298, 300.1, 306, 312, 317.2, 317.3; 435/410, 419, 421, 430, 468; 536/23.1, 23.6, 24.5

(56) References Cited

PUBLICATIONS

Roberts et al., Fusicoccin, 14–3–3 Proteins and Defense Responses in Tomato Plants. Plant Physiology (1999); vol. 119, pp. 1243–1250.*
Wu K. et al., Plant Physiology, 1997, vol. 114, pp. 1342–1431.*
Elomaa P. et al., Molecular Breeding 1996, vol. 2, pp. 41–50.*
Waterhouse P. et al., Trends in Plant Sciences, Nov. 1999, vol. 4, No. 11 pp. 452–457.*
Smith C. et al., Nature 1988, 334: 724–726.*
Wilczynski G. et al. J. of Plant Physiol, 1998, vol. 153, pp. 118–126.*
Gordon–Kamm et al. The Plant Cell, Jul. 1990, vol. 2, pp. 603–618.*
Ferl et al. GenBank Accession No. U36446, submitted Sep. 15, 1995.*
Ferl et al. GenBank Accession No. U60444, submitted Jun. 11, 1996.*
Wilczynski G. et al., J. of Pl. Phsiol., 1997, vol. 151, pp. 689–698.*

Altschul, S. F., et al., "Gapped BLAST and PSI–BLAST: A New Generation of Protein Database Search Programs" *Nucleic Acids Research,* 1997, pp. 3389–3402, vol. 25, No. 17, Oxford University Press.
Bachmann, M. et al. "The Inhibitor Protein of Phosphorylated Nitrate Reductase from Spinach (*Spinacia Oleracea*) Leaves in a 14–3–3 Protein" *FEBS Letters,* 1996, pp. 127–131, vol. 387.
Bechtold, N. et al. "*In Planta Agrobacterium*–Mediated Transformation of Adult *Arabidopsis Thaliana* Plants by Vacuum Infiltration" *Methods in Molecular Biology,* 1998, pp. 259–266, vol. 82, Humana Press Inc., Totowa, NJ.
Bihn, E. A. et al. "Localization of 14–3–3 Poteins in the Nuclei of Arabidopsis and Maize" *The Plant Journal,* 1997, pp. 1439–1445, vol. 12, No. 6.
Cao, H. et al., "Identification of the Soluble Starch Synthase Activities of Maize Endosperm" *Plant Physiology,* 1999, pp. 205–215, vol. 120.
Chung, H. J. et al. "The 14–3–3 Proteins: Cellular Regulators of Plant Metabolism" *Trends in Plant Science,* 1999, pp. 367–371, vol. 4.
Craig, J. et al. "Mutations in the Gene Encoding Starch Synthase II Profoundly Alter Amylopectin Structure in Pea Embryos" *The Plant Cell,* 1998, pp. 413–426, vol. 10.
Daugherty, C. J. et al. "Molecular Organization and Tissue–Specific Expression of an Arabidopsis 14–3–3 Gene" *The Plant Cell,* 1996, pp. 1239–1248, vol. 8.
De Vetten N. C. et al. "Two Genes Encoding GF14 (14–3–3) Proteins in *Zea mays*" *Plant Physiology,* 1994, pp. 1593–1604, vol. 106.

(List continued on next page.)

*Primary Examiner*—David T. Fox
*Assistant Examiner*—Russell Kallis
(74) *Attorney, Agent, or Firm*—Saliwanchik, Lloyd & Saliwanchik

(57) ABSTRACT

The subject invention concerns materials and methods for enhancing starch production in plants. Starch production is enhanced, relative to levels observed in wildtype or control plants, by reduction of the plant 14-3-3 protein(s) which subsequently results in increased accumulation of starch in the plant. In one embodiment, the 14-3-3 protein expression is reduced using polynucleotides that are antisense to the 14-3-3 gene sequences expressed in the plant. In another embodiment, the 14-3-3 protein expression is reduced by "knockout" of a 14-3-3 gene or gene sequences. The subject invention also pertains to transformed and transgenic plants that have polynucleotides that are antisense to the 14-3-3 gene sequences expressed in the plant, wherein the transformed and transgenic plants exhibit enhanced starch production. The subject invention also pertains to "knockout" plants in which the normal functional 14-3-3 gene in the plant is deleted or replaced with a non-functional form of the gene. The subject invention also concerns the "antisense" polynucleotides of the invention that when introduced into a plant cell can function to effectively reduce expression of the 14-3-3 proteins in a plant.

20 Claims, 3 Drawing Sheets

PUBLICATIONS

Edwards, A. et al. "A Combined Reduction in Activity of Starch Synthases II and III of Potato has Novel Effects on the Starch of Tubers" *The Plant Journal,* 1999, pp. 251–261, vol. 17, No. 3.

Holsters, M. et al. "Transfection and Transformation of *Agrobacterium Tumefaciens*" *Molec. Gen. Genet.,* 1978, pp. 181–187, vol. 163.

Imparl–Radosevich, J. M., et al. "Analysis of Purified Maize Starch Synthases lla and llb: SS Isoforms Can Be Distinguished Based on Their Kinetic Properties" *Archives of Biochemistry and Biophysics,* 1999, pp. 131–138, vol. 362, No. 1.

Konishi, Y. et al. "Characterization of Starch Granules from Waxy, Nonwaxy, and Hybrid Seeds of *Amaranthus hypochondriacus* L." *Agric. Biol. Chem.,* 1985, pp. 1965–1971, vol. 49, No. 7.

Krysan, P. J. et al. "Identification of Transferred DNA Insertions Within *Arabidopsis* Genes Involved in Signal Transduction and Ion Transport" *Proc. Natl. Acad. Sci. USA,* 1996, pp. 8145–8150, vol. 93.

Lloyd, J. R. et al. "Simultaneous Antisense Inhibition of Two Starch–Synthase Isoforms in Potato Tubers Leads to Accumulation of Grossly Modified Amylopectin" *Biochem. J.,* 1999, pp. 515–521, vol. 338.

MacDonald, F. D. et al. "Solubilization of the Starch–Granule–Bound Starch Synthase of Normal Maize Kernels" *Plant Physiology,* 1983, pp. 175–178, vol. 73.

Moorhead, G. et al. "Phosphorylated Nitrate Reductase From Spinach Leaves is Inhibited by 14–3–3 Proteins and Activated by Fusicoccin" *Current Biology,* 1996, pp. 1104–1113, vol. 6, No. 9.

Moorhead, G. et al. "Phosphorylation–dependent Interactions Between Enzymes of Plant Metabolism and 14–3–3 Proteins" *The Plant Journal,* 1999, pp. 1–12, vol. 18, No. 1.

Mu–Forster, C. et al. "Physical Association of Starch Biosynthetic Enzymes with Starch Granules of Maize Endosperm" *Plant Physiology,* 1996, pp. 821–829, vol. 111.

Mu–Forster, C. et al. "Surface Localization of Zein Storage Proteins in Starch Granules from Maize Endosperm" *Plant Physiology,* 1998, pp. 1563–1571, vol. 116.

Preiss, J. et al. "Biochemistry, Molecular Biology and Regulation of Starch Synthesis" *Genetic Engineering,* 1998, pp. 177–223, vol. 20.

Sehnke, P. C. et al. "Interaction of a Plant 14–3–3 Protein with the Signal Peptide of a Thylakoid–Targeted Chloroplast Precursor Protein and the Presence of 14–3–3 Isoforms in the Chloroplast Stroma" *Plant Physiology,* 2000, pp. 235–241, vol. 122.

Sehnke, P. C. et al. "Plant Metabolism: Enzyme Regulation by 14–3–3 Proteins" *Current Biology,* 1996, pp. 1403–1405, vol. 6, No. 11.

Sehnke, P. C. et al. "Regulation of Starch Accumulation by Granule–Associated Plant 14–3–3 Proteins" *Proc. Natl. Acad. Sci. USA,* 2001, pp. 765–770, vol. 98. Also published online (www.pnas.org/cgi/doi/10.1073/pnas.021304198) before print on Jan. 9, 2001.

Smith, A. M. "Making Starch" *Current Opinion in Plant Biology,* 1999, pp. 223–229, vol. 2.

Sokolov, L. N. et al. "Sugars and Light/Dark Exposure Trigger Differential Regulation of ADP–Glucose Pyrophosphorylase Genes in *Arabidopsis Thaliana* (Thale Cress)" *Biochem. J.,* 1998, pp. 681–687, vol. 336.

Sun, J. et al. "Modification of Carbon Partitioning, Photosynthetic Capacity, and $O_2$ Sensitivity in Arabidopsis Plants with Low ADP–Glucose Pyrophosphorylase Activity" *Plant Physiology,* 1999, pp. 267–276, vol. 119.

Toroser, D. et al. "Site–Specific Regulatory Interaction Between Spinach Leaf Sucrose–Phosphate Synthase and 14–3–3 Proteins" *FEBS Letters,* 1998, pp. 110–114, vol. 435.

Wu, K. et al. "The Arabidopsis 14–3–3 Multigene Family" *Plant Physiology,* 1997, pp. 1421–1431, vol. 114.

Zeeman, S. C. et al. "A Starch–Accumulating Mutant of *Arabidopsis Thaliana* Deficient in a Chloroplastic Starch––Hydrolysing Enzyme" *The Plant Journal,* 1998, pp. 357–365, vol. 15, No. 3.

* cited by examiner

FIG. 1A FIG. 1B FIG. 1C
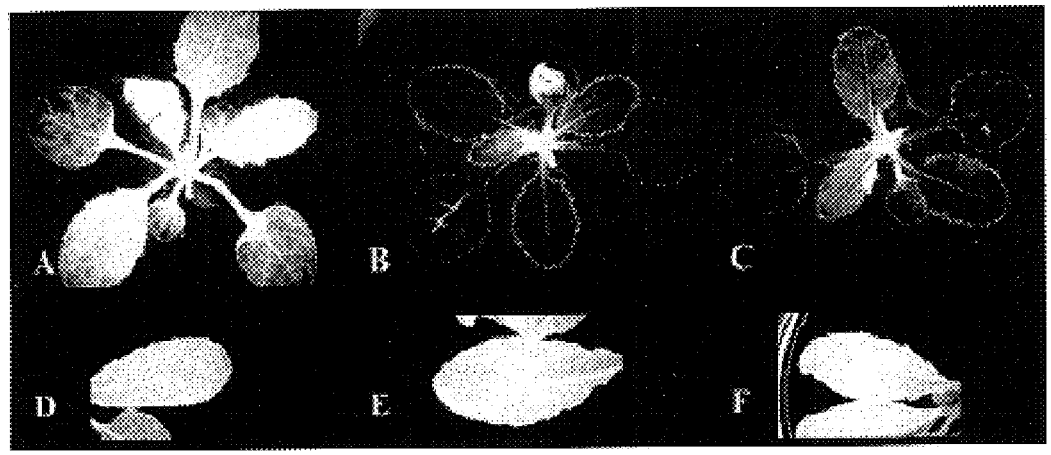
FIG. 1D FIG. 1E FIG. 1F
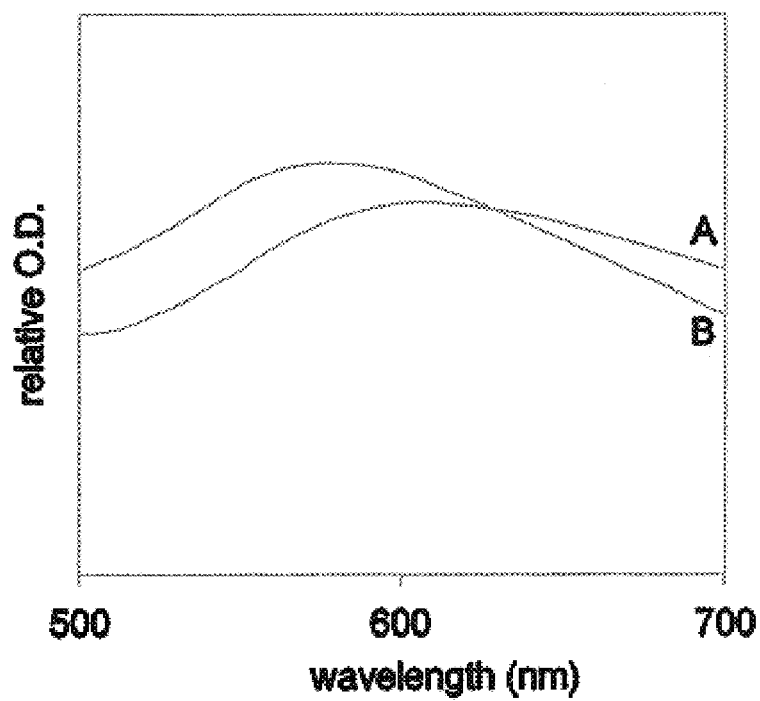
FIG. 2

1   2   3   4   5

```
14-3-3 CONSENSUS BD            RXX(S/T)XP

NR 14-3-3 BD          540  lkRTA(S)TPfm
Potato SSIII         1333  amRYG(S)IPvv
Dull1 SS             1578  amRYG(T)IPiv
Vigna SSIII          1050  amRYG(S)IPiv
Triticum SSIII       1530  amRYG(S)IPiv
Aegilops SSIII       1513  amRYG(S)IPiv
At SSIII              943  amRYG(S)IPia
```

SEQUENCE LISTING

```
<160> NUMBER OF SEQ ID NOS: 4

<210> SEQ ID NO 1
<211> LENGTH: 1100
<212> TYPE: DNA
<213> ORGANISM: Arabidopsis sp.
<220> FEATURE:
<221> NAME/KEY: CDS
<222> LOCATION: (49)..(810)

<400> SEQUENCE: 1
gcggccgcgt cgacgaagga agaagaagaa gaagaagaag aaaaaact atg gag aat         57
                                                    Met Glu Asn
                                                    1 gag agg gaa aag cag gtt tac ttg gct aag ctc tcc gag caa acc gaa        105
Glu Arg Glu Lys Gln Val Tyr Leu Ala Lys Leu Ser Glu Gln Thr Glu
    5                  10                  15 aga tac gat gaa atg gtg gag gcg atg aag aaa gtt gct cag ctt gat        153
Arg Tyr Asp Glu Met Val Glu Ala Met Lys Lys Val Ala Gln Leu Asp
20                  25                  30                  35 gtg gag cta act gtg gaa gag agg aat ctt gta tct gta ggg tac aag        201
Val Glu Leu Thr Val Glu Glu Arg Asn Leu Val Ser Val Gly Tyr Lys
```

-continued

```
                        40                  45                  50
aat gtg att ggt gca agg aga gca tca tgg aga ata cta tct tcc att     249
Asn Val Ile Gly Ala Arg Arg Ala Ser Trp Arg Ile Leu Ser Ser Ile
             55                  60                  65 gag cag aag gaa gag tcc aag gga aat gat gaa aat gtc aag agg ctt     297
Glu Gln Lys Glu Glu Ser Lys Gly Asn Asp Glu Asn Val Lys Arg Leu
         70                  75                  80 aag aat tat cgt aag aga gtt gaa gat gag ctt gct aaa gtt tgt aat     345
Lys Asn Tyr Arg Lys Arg Val Glu Asp Glu Leu Ala Lys Val Cys Asn
     85                  90                  95 gac atc ttg tct gtc att gat aag cat ctc att cca tcg tct aac gct     393
Asp Ile Leu Ser Val Ile Asp Lys His Leu Ile Pro Ser Ser Asn Ala
100                 105                 110                 115 gtg gag tca act gtc ttt ttc tac aaa atg aaa gga gat tac tat cgc     441
Val Glu Ser Thr Val Phe Phe Tyr Lys Met Lys Gly Asp Tyr Tyr Arg
                    120                 125                 130 tat ctt gcg gag ttc agt tct ggt gct gaa cgc aag gaa gct gca gat     489
Tyr Leu Ala Glu Phe Ser Ser Gly Ala Glu Arg Lys Glu Ala Ala Asp
                135                 140                 145 cag tct ctt gaa gca tat aag gct gct gtt gct gct gca gag aat ggt     537
Gln Ser Leu Glu Ala Tyr Lys Ala Ala Val Ala Ala Ala Glu Asn Gly
            150                 155                 160 ttg gca ccc aca cat cca gtt aga ctt ggc ttg gcg ttg aac ttt tca     585
Leu Ala Pro Thr His Pro Val Arg Leu Gly Leu Ala Leu Asn Phe Ser
        165                 170                 175 gtt ttc tac tat gag atc ttg aac tct ccc gaa agc gca tgc caa ttg     633
Val Phe Tyr Tyr Glu Ile Leu Asn Ser Pro Glu Ser Ala Cys Gln Leu
180                 185                 190                 195 gct aag caa gca ttc gat gat gca att gct gaa ctt gac agc ctc aac     681
Ala Lys Gln Ala Phe Asp Asp Ala Ile Ala Glu Leu Asp Ser Leu Asn
                    200                 205                 210 gag gaa tca tac aaa gac agc act ctt att atg cag cta ctt aga gac     729
Glu Glu Ser Tyr Lys Asp Ser Thr Leu Ile Met Gln Leu Leu Arg Asp
                215                 220                 225 aat ctc acc ttg tgg act tca gac ctt aat gag gaa gga gat gag aga     777
Asn Leu Thr Leu Trp Thr Ser Asp Leu Asn Glu Glu Gly Asp Glu Arg
            230                 235                 240 acc aaa ggt gct gat gag cct caa gat gag aac taaatcctct gtgagaagag   830
Thr Lys Gly Ala Asp Glu Pro Gln Asp Glu Asn
        245                 250 aaacgactct tgctgcatcc tgaatcttga agtgaagaca gtaagtgtcg ttgtttgtta   890
ctcgaatgtg taattttaa tctatgtctt tcttgatggt gttttccaga ttcttgaact    950
tttcacaaca caacactgcg ttgcgtatct tcaaccctct tatgatgtgg ttgaattctg  1010
ttttacgctt agtttgcttc tttgttgtt gaattgagcc agcaggcatg atttgggttt  1070
ttgtttatca gaatattagg cgtaaaaaaa                                   1100
```

<210> SEQ ID NO 2
<211> LENGTH: 254
<212> TYPE: PRT
<213> ORGANISM: Arabidopsis sp.

<400> SEQUENCE: 2

```
Met Glu Asn Glu Arg Glu Lys Gln Val Tyr Leu Ala Lys Leu Ser Glu
1               5                   10                  15

Gln Thr Glu Arg Tyr Asp Glu Met Val Glu Ala Met Lys Lys Val Ala
            20                  25                  30

Gln Leu Asp Val Glu Leu Thr Val Glu Glu Arg Asn Leu Val Ser Val
```

-continued

```
             35                  40                  45
Gly Tyr Lys Asn Val Ile Gly Ala Arg Arg Ala Ser Trp Arg Ile Leu
     50                  55                  60

Ser Ser Ile Glu Gln Lys Glu Ser Lys Gly Asn Asp Glu Asn Val
65                  70                  75                  80

Lys Arg Leu Lys Asn Tyr Arg Lys Val Glu Asp Glu Leu Ala Lys
                 85                  90                  95

Val Cys Asn Asp Ile Leu Ser Val Ile Asp Lys His Leu Ile Pro Ser
                100                 105                 110

Ser Asn Ala Val Glu Ser Thr Val Phe Phe Tyr Lys Met Lys Gly Asp
                115                 120                 125

Tyr Tyr Arg Tyr Leu Ala Glu Phe Ser Ser Gly Ala Glu Arg Lys Glu
        130                 135                 140

Ala Ala Asp Gln Ser Leu Glu Ala Tyr Lys Ala Val Ala Ala Ala
145                 150                 155                 160

Glu Asn Gly Leu Ala Pro Thr His Pro Val Arg Leu Gly Leu Ala Leu
                165                 170                 175

Asn Phe Ser Val Phe Tyr Tyr Glu Ile Leu Asn Ser Pro Glu Ser Ala
                180                 185                 190

Cys Gln Leu Ala Lys Gln Ala Phe Asp Asp Ala Ile Ala Glu Leu Asp
        195                 200                 205

Ser Leu Asn Glu Glu Ser Tyr Lys Asp Ser Thr Leu Ile Met Gln Leu
    210                 215                 220

Leu Arg Asp Asn Leu Thr Leu Trp Thr Ser Asp Leu Asn Glu Glu Gly
225                 230                 235                 240

Asp Glu Arg Thr Lys Gly Ala Asp Glu Pro Gln Asp Glu Asn
                245                 250
```

<210> SEQ ID NO 3
<211> LENGTH: 1113
<212> TYPE: DNA
<213> ORGANISM: Epsilon
<220> FEATURE:
<221> NAME/KEY: CDS
<222> LOCATION: (70)..(858)

<400> SEQUENCE: 3

```
agtaatttag gtcgtcaaaa gctttggaat ttgatacttt tgattttcg agaatcttga         60 aaatcagtc atg ggt tct gga aaa gag cgt gac act ttc gtc tac ctc gct       111
          Met Gly Ser Gly Lys Glu Arg Asp Thr Phe Val Tyr Leu Ala
            1               5                  10 aag ctc tct gag caa gct gag cgt tat gaa gaa atg gtg gaa tca atg         159
Lys Leu Ser Glu Gln Ala Glu Arg Tyr Glu Glu Met Val Glu Ser Met
15                  20                  25                  30 aaa agt gtt gcg aaa ttg aat gtt gat ctg acg gtg gaa gag agg aac         207
Lys Ser Val Ala Lys Leu Asn Val Asp Leu Thr Val Glu Glu Arg Asn
                35                  40                  45 tta ctc tct gtg ggt tac aag aac gtg att ggt tca agg aga gct tcg         255
Leu Leu Ser Val Gly Tyr Lys Asn Val Ile Gly Ser Arg Arg Ala Ser
         50                  55                  60 tgg agg atc ttc tcg tcg att gaa caa aag gaa gca gtg aaa ggg aat         303
Trp Arg Ile Phe Ser Ser Ile Glu Gln Lys Glu Ala Val Lys Gly Asn
65                  70                  75 gat gtt aat gta aag agg atc aaa gag tat atg gag aag gtt gag tta         351
Asp Val Asn Val Lys Arg Ile Lys Glu Tyr Met Glu Lys Val Glu Leu
        80                  85                  90 gag ctt tct aac ata tgc att gat att atg tct gtc tta gat gag cat         399
```

-continued

| | | |
|---|---|---|
| Glu Leu Ser Asn Ile Cys Ile Asp Ile Met Ser Val Leu Asp Glu His<br>95                          100                 105                   110 | | |
| ctc att cct tcg gct tcc gag ggt gaa tct act gtc ttc ttc aac aag<br>Leu Ile Pro Ser Ala Ser Glu Gly Glu Ser Thr Val Phe Phe Asn Lys<br>                  115                   120                   125 | 447 | |
| atg aaa ggt gac tat tac cgc tat ctt gct gag ttc aaa tca ggg aac<br>Met Lys Gly Asp Tyr Tyr Arg Tyr Leu Ala Glu Phe Lys Ser Gly Asn<br>130                          135                    140 | 495 | |
| gag agg aaa gag gct gct gat cag tct ttg aaa gcc tat gag att gct<br>Glu Arg Lys Glu Ala Ala Asp Gln Ser Leu Lys Ala Tyr Glu Ile Ala<br>      145                       150                   155 | 543 | |
| act act gct gct gag gct aag ctc cct cca aca cac cct atc aga ttg<br>Thr Thr Ala Ala Glu Ala Lys Leu Pro Pro Thr His Pro Ile Arg Leu<br>160                          165                   170 | 591 | |
| ggt ttg gct ttg aat ttc tct gtc ttc tac tac gag atc atg aac gca<br>Gly Leu Ala Leu Asn Phe Ser Val Phe Tyr Tyr Glu Ile Met Asn Ala<br>175                          180                   185                   190 | 639 | |
| cct gaa agg gca tgt cac ctt gct aag cag gcg ttc gat gaa gct atc<br>Pro Glu Arg Ala Cys His Leu Ala Lys Gln Ala Phe Asp Glu Ala Ile<br>                  195                   200                   205 | 687 | |
| tca gag ctt gac act ctg agc gag gaa tcc tac aaa gat agc acc tta<br>Ser Glu Leu Asp Thr Leu Ser Glu Glu Ser Tyr Lys Asp Ser Thr Leu<br>210                          215                    220 | 735 | |
| ata atg caa ctc ctt agg gac aat ctg acc ttg tgg act tct gac atc<br>Ile Met Gln Leu Leu Arg Asp Asn Leu Thr Leu Trp Thr Ser Asp Ile<br>      225                       230                   235 | 783 | |
| tca gaa gaa gga gga gac gat gct cat aag acg aat ggt tct gcc aaa<br>Ser Glu Glu Gly Gly Asp Asp Ala His Lys Thr Asn Gly Ser Ala Lys<br>240                          245                   250 | 831 | |
| cct ggt gct ggt gga gac gat gca gag tgatatgata tgtgtgcacc<br>Pro Gly Ala Gly Gly Asp Asp Ala Glu<br>255                          260 | 878 | |
| tggacaatat gtttcaagaa ctgaatgtgc ggtgaataat agtgaaaagt agagtttctc | 938 | |
| tgttccctat atcatgattg tctatgttac ttgtactctg gtttagccct aaatgtctct | 998 | |
| ctggtttgaa tgtattgcat gcctgtctca ggacactctt atttgtaatt cactactgtc | 1058 | |
| gtcctactat ctatccttat ggatccaatc ttgaaactaa aaaaaaaaaa aaaaa | 1113 | |

<210> SEQ ID NO 4
<211> LENGTH: 263
<212> TYPE: PRT
<213> ORGANISM: Epsilon

<400> SEQUENCE: 4

Met Gly Ser Gly Lys Glu Arg Asp Thr Phe Val Tyr Leu Ala Lys Leu
1                  5                      10                     15

Ser Glu Gln Ala Glu Arg Tyr Glu Glu Met Val Glu Ser Met Lys Ser
                    20                      25                     30

Val Ala Lys Leu Asn Val Asp Leu Thr Val Glu Glu Arg Asn Leu Leu
             35                      40                      45

Ser Val Gly Tyr Lys Asn Val Ile Gly Ser Arg Arg Ala Ser Trp Arg
50                          55                      60

Ile Phe Ser Ser Ile Glu Gln Lys Glu Ala Val Lys Gly Asn Asp Val
65                   70                      75                     80

Asn Val Lys Arg Ile Lys Glu Tyr Met Glu Lys Val Glu Leu Glu Leu
                      85                      90                     95

Ser Asn Ile Cys Ile Asp Ile Met Ser Val Leu Asp Glu His Leu Ile
                  100                   105                   110

```
Pro Ser Ala Ser Glu Gly Glu Ser Thr Val Phe Phe Asn Lys Met Lys
        115                 120                 125
Gly Asp Tyr Tyr Arg Tyr Leu Ala Glu Phe Lys Ser Gly Asn Glu Arg
    130                 135                 140
Lys Glu Ala Ala Asp Gln Ser Leu Lys Ala Tyr Glu Ile Ala Thr Thr
145                 150                 155                 160
Ala Ala Glu Ala Lys Leu Pro Pro Thr His Pro Ile Arg Leu Gly Leu
                165                 170                 175
Ala Leu Asn Phe Ser Val Phe Tyr Tyr Glu Ile Met Asn Ala Pro Glu
                180                 185                 190
Arg Ala Cys His Leu Ala Lys Gln Ala Phe Asp Glu Ala Ile Ser Glu
        195                 200                 205
Leu Asp Thr Leu Ser Glu Glu Ser Tyr Lys Asp Ser Thr Leu Ile Met
    210                 215                 220
Gln Leu Leu Arg Asp Asn Leu Thr Leu Trp Thr Ser Asp Ile Ser Glu
225                 230                 235                 240
Glu Gly Gly Asp Asp Ala His Lys Thr Asn Gly Ser Ala Lys Pro Gly
                245                 250                 255
Ala Gly Gly Asp Asp Ala Glu
                260
```

US 6,867,350 B2

PLANTS WITH ENHANCED ABILITY TO PRODUCE STARCH AND METHODS FOR OBTAINING THEM

CROSS-REFERENCE TO RELATED APPLICATION

This application claims the benefit of U.S. Provisional Application No. 60/204,746, filed May 17, 2000.

The subject invention was made with government support under a research project supported by USDA NRI Grant Nos. 00-35304-9601 and 97-35304-4942. The government has certain rights in this invention.

BACKGROUND OF THE INVENTION

Carbon and nitrogen apportioning in plants has a direct impact on their usefulness as agricultural commodities. Research directed toward altered regulation and reallocation of these assimilates represents a major effort in agricultural biology at both the biochemical and genetic levels. Several key enzymes in the metabolic pathways that direct carbon and nitrogen flow, process assimilates, and transfer the products into various sink tissues are of intense investigative interest. The biosynthesis of starch is one such well-regulated diurnal process (Smith, 1999; Preiss et al., 1998), with starch serving as a major carbon reserve as well as an energy source for plants and providing a major nutritional value of food crops. The dynamic throughput of plant carbon demands a tight, yet responsive, control of the key enzymes. To further add to the complexity, starch production occurs exclusively in membrane-bound plastids, thereby requiring import of the biosynthetic enzymes and regulators involved. However, localization within the plastid also serves to essentially distinguish enzymes directly involved in starch synthesis and therefore identify potential targets for genetic manipulation.

Starch is synthesized in leaves during the day from photosynthetically assimilated carbon derived via the reductive pentose phosphate pathway. One simple view of starch polymer production involves four types of enzymes: ADP-glucose pyrophosphorylase (AGP), starch synthases (SSs), starch-branching enzymes (SBEs), and starch-debranching enzymes (DBEs) (Smith, 1999). AGP forms ADP-glucose from glucose 1-phosphate. SSs add ADP-glucose to the elongating end of an $\alpha(1-4)$-linked glucanchain, whereas SBEs cut $\alpha(1-4)$ links and rejoin them as $\alpha(1-6)$ branches that are subsequently trimmed by DBEs to yield short chains for further synthetic extension. However, different isoforms of SSs (soluble and granule-associated SSI, SSII, and SSIII) can participate in the production of branched glucans. For example, the granule-bound SSI, the waxy-encoded protein in maize, is directly and perhaps exclusively involved in producing amylose, an $\alpha(1-4)$ glucan polymer with little branching. In contrast, SSII participates in the synthesis of amylopectin, an $\alpha(1-6)$ branched glucan polymer that typically is found together with amylose to form starch granules. The ratio of these two glucans affects the physical characteristics of starch such as gelatinization and the absorption spectra of iodine-complexed starch. The alteration or absence of certain starch biosynthetic enzymes (Craig et al. 1998; Edwards et al. 1999; Lloyd et al. 1999) has a dramatic effect on the physical characteristics of starch, as well as the level of starch accumulated by the plant. In a similar, yet opposing, manner dark-regulated starch degradation occurs by means of catabolic enzymes such as amylase, $\alpha$-glucosidase, and starch phosphorylase. The resulting starch stasis is the consequence of the metabolism and catabolism orchestrated by the respective enzymes.

Regulation of some enzymes involved in major resource allocation is affected by allosteric effectors, substrate levels, and product levels, as well as by phosphorylation (Sokolov et al., 1998; Sun et al., 1999; Imparl-Radosevich et al., 1999). For several key enzymes, regulation of activity is a two-step process involving phosphorylation of the enzyme, followed by formation of a complex with 14-3-3 proteins to complete the regulatory transition (Chung et al., 1999; Sehnke et al., 1997). For example, the assimilation of nitrogen for production of amino acids or nucleotide bases is tightly controlled by nitrate reductase (NR). NR responds to environmental signals, such as light and metabolite levels, by phosphorylation and interacts with 14-3-3 proteins (Bachmann et al, 1996; Moorhead et al., 1996), thereby rapidly altering nitrogen flux according to the plant's metabolic requirements. This phosphorylation-dependent interaction of NR with 14-3-3 proteins has become a paradigm for posttranslational regulation of metabolic enzymes (Chung et al., 1999). Recently, 14-3-3 proteins have been identified inside plastids (Sehnke et al., 2000), thereby implicating a potential role in starch regulation.

Several methods have previously been suggested for modifying the ability of plants to produce and store starch. See, e.g., U.S. Pat. No. 5,365,016; 5,498,831; 5,789,657; 5,792,920; 5,824,798; 5,830,724; 5,856,467; 5,959,180; 5,962,769; 5,981,852; 5,998,701; and 6,013,861.

BRIEF SUMMARY OF THE INVENTION

The subject invention concerns materials and methods for enhancing starch production in plants. Starch production is enhanced, relative to levels observed in wildtype or control plants, by reduction of the activity of plant 14-3-3 protein(s) which subsequently results in increased accumulation of starch in the plant. In one embodiment, the 14-3-3 protein expression is reduced using polynucleotides that are antisense to the 14-3-3 gene sequences expressed in the plant. In another embodiment, the 14-3-3 protein expression is reduced by "knockout" of a 14-3-3 gene or gene sequences.

Methods of the present invention for enhancing starch production in a plant include introducing into the plant a polynucleotide of the invention that comprises a nucleotide sequence that is antisense to the 14-3-3 DNA or RNA sequences in the plant. Another method of the invention concerns deleting or replacing the functional 14-3-3 genes in a plant with a non-functional form of the gene.

The subject invention also pertains to transformed and transgenic plants that have polynucleotides that are antisense to the 14-3-3 gene sequences expressed in the plant, wherein the transformed and transgenic plants exhibit enhanced starch production.

The subject invention also pertains to "knockout" plants which exhibit enhanced starch production, wherein the normal functional 14-3-3 gene in the plant is deleted or replaced with a non-functional form of the gene.

The subject invention also concerns the "antisense" polynucleotides of the invention that when introduced into a plant cell can function to effectively reduce expression of the 14-3-3 proteins in a plant.

BRIEF DESCRIPTION OF THE DRAWINGS

FIGS. 1A–1F show starch accumulation in transgenic GF14 antisense plants. Starch levels in wild-type (FIG. 1A) and GF14 $\epsilon$ and (FIG. 1B) and $\mu$ (FIG. 1C) antisense plants grown under constant light were assayed by iodine staining. The density of staining clearly indicates increased starch levels in the leaves of antisense plants. Identical photographic lighting and exposure conditions were used for FIGS. 1A–1C so that the intensities of the staining are directly comparable. Similar plants were subjected to an 18-h dark period to allow for starch degradation before staining (FIGS. 1D, 1E, and 1F, respectively), and the results indicate that starch degradation is uninhibited in the 14-3-3 antisense plants.

FIG. 2 shows altered starch composition of antisense starch granules. The absorption spectra of iodine/starch complexes of wild-type (FIG. 2, spectrum A) and 14-3-3 antisense (FIG. 2, spectrum B) *Arabidopsis* starch granules indicate that the 14-3-3ε antisense plants contain an increase in the relative content of branched glucans.

BRIEF DESCRIPTION OF THE SEQUENCES

Figures 3A, 3B, 3C:
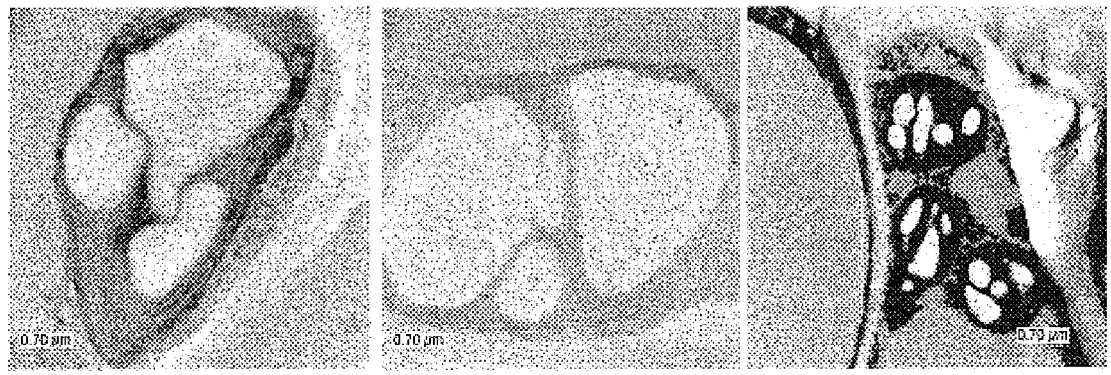
FIGS. 3A–3C show immunolocalization of 14-3-3 proteins in starch granules. *Arabidopsis* leaves were processed for electron microscopy (Bihn et al., 1997) and immunolabeled with GF14 antibodies. Control antibodies to *Dictyostelium* spores (FIG. 3A) did not immunodecorate the granules; however, antibodies that recognize both ε (FIG. 3C) and non-ε (FIG. 3B) 14-3-3 proteins were concentrated inside the starch granules.

SEQ ID NO. 1 is a polynucleotide sequence encoding 14-3-3 Epsilon protein.

SEQ ID NO. 2 is an amino acid sequence of a 14-3-3 Epsilon protein encoded by the polynucleotide sequence shown in SEQ ID NO. 1.

SEQ ID NO. 3 is a polynucleotide sequence encoding 14-3-3 Mu protein.

SEQ ID NO. 4 is an amino acid sequence of a 14-3-3 Mu protein encoded by the polynucleotide sequence shown in SEQ ID NO. 3.

DETAILED DISCLOSURE OF THE INVENTION

The subject invention concerns materials and methods for enhancing starch production in plants. Starch production is enhanced, relative to levels observed in wildtype or control plants, by reduction of the activity of plant 14-3-3 protein(s) which subsequently results in increased accumulation of starch in the plant. It has been discovered that the 14-3-3 proteins function as inhibitory proteins in starch metabolism by shutting down starch metabolism. It has also been discovered, based on the presence of 14-3-3 consensus binding domains and biochemical experiments, that one target of the granule 14-3-3 proteins is the SSIII family of enzymes.

One method for enhancing starch production in a plant comprises introducing into the plant a polynucleotide of the invention that comprises a nucleotide sequence that is antisense to a 14-3-3 gene sequence in the plant. In one embodiment, a DNA molecule encoding an RNA molecule that hybridizes to an mRNA molecule that encodes a 14-3-3 protein is introduced into a plant. The mRNA molecule may encode, for example, a 14-3-3 protein having an amino acid sequence disclosed in SEQ ID NO. 2 or SEQ ID NO. 4.

Another method for enhancing starch production by inhibiting 14-3-3 protein expression in a plant comprises deleting or replacing a functional 14-3-3 gene with a non-functional gene. The plant in which the functional gene has been deleted or non-functionalized is referred to as a "knockout" plant. General methods for producing "knockout" plants are known and have been described in the art (See, e.g., Krysan et al., 1996).

Methods for enhancing starch production in a plant contemplated by the present invention also include direct inhibition of the 14-3-3 proteins in plants. In one embodiment, a plant is transformed with a polynucleotide that encodes an antibody, or a functional fragment thereof, e.g., an Fv portion of the antibody, that binds to and blocks the function of the 14-3-3 proteins. In another embodiment, a plant is transformed with a polynucleotide that provides an aptamer that can bind to and inhibit the function of the 14-3-3 proteins in the plant. As used herein, the term "aptamer" refers to a polynucleotide or polypeptide that has the ability to bind with a high degree of affinity and specificity to a target protein molecule. The expression of antibodies or aptamers directed to 14-3-3 proteins can be selected to be inducible or constitutive in the transformed or transgenic plant.

The subject invention also concerns the "antisense" polynucleotides of the invention that when introduced into a plant cell can function to effectively reduce expression of the 14-3-3 proteins in a plant. In one embodiment, a polynucleotide of the invention comprises a DNA molecule encoding an RNA molecule that can hybridize to an mRNA molecule that encodes a 14-3-3 protein a plant. The mRNA molecule may encode, for example, a 14-3-3 protein having an amino acid sequence disclosed in SEQ ID NO. 2 or SEQ ID NO. 4.

The subject invention also pertains to transformed and transgenic plants that have polynucleotides that are antisense to the 14-3-3 gene sequences expressed in the plant, wherein the transformed and transgenic plants exhibit enhanced starch production. In one embodiment, a DNA molecule encoding an RNA molecule that hybridizes to an mRNA molecule that encodes a 14-3-3 protein is introduced into a plant. The mRNA molecule may encode, for example, a 14-3-3 protein having an amino acid sequence disclosed in SEQ ID NO. 2 or SEQ ID NO.4.

The subject invention also pertains to "knockout" plants which exhibit enhanced starch production, wherein the normal functional 14-3-3 gene in the plant is deleted or replaced with a non-functional form of the gene.

In one embodiment, a polynucleotide according to the present invention is inserted into a suitable vector, and the recombinant vector is used to transform a bacterium or other host which can then be used to introduce the polynucleotide into a plant cell. *Agrobacterium* containing a polynucleotide of the invention can be used to transform plant cells with the polynucleotide according to standard methods known in the art. Polynucleotides of the present invention can also be introduced into plant cells using a biolistic method (Carrer, 1995), as well as by other methods known in the art, such as electroporation, microinjection and virus-mediated transformation.

Transformed, transgenic and knockout plants produced according to the present invention include both monocot and dicot plants. Dicot plants contemplated within the scope of the present invention include, for example, tobacco, potato, cabbage, soybeans, and sweet potato. Monocot plants contemplated within the scope of the invention include, for example, maize, wheat, barley, rice, oats and other small cereals. In a preferred embodiment, the maize is *Zea mays*. In an exemplified embodiment, the plant is *Arabidopsis*.

Also contemplated within the scope of the invention is plant material, including plant tissue, seeds, plant cells and protoplasts, from the transformed, transgenic or "knockout" plants of the present invention.

As used herein, the terms "nucleic acid" and "polynucleotide sequence" refer to a deoxyribonucleotide or ribonucleotide polymer in either single- or double-stranded form, and unless otherwise limited, includes polynucleotides containing known analogs of natural nucleotides that can function in a similar manner as naturally-occurring nucleotides.

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Materials and Methods

Antisense GF14 Vector Construction and Transformation into *Arabidopsis*. Clones for the *Arabidopsis* 14-3-3 proteins GF14 ε and GF14 μ, from yeast two-hybrid vectors (Wu et al., 1997), were used as templates for PCR to produce XbαI cassettes that were subsequently subcloned into the binary plant transformation vector pBI121 (CLONTECH). Gene orientation was determined by automated DNA sequencing on a Perkin-Elmer ABI 373A. Clones containing the antisense GF14 gene orientation were amplified in *Escherichia coli* INVαF' and used to transform competent *Agrobacterium tumefaciens* strain EHA105 by the freeze-thaw method (Holsters et al., 1978). The vector-harboring *Agrobacterium* was used to transform *Arabidopsis* ecotype WS seedlings by using vacuum infiltration, essentially as described by Bechtold and Pelletier (Bechtold et al., 1998). Transformants were screened on germination media plates using 40 μg/ml kanamycin selection as described previously (Daugherty et al., 1996). Seed from positive transformants were selected through three successive generations to ensure homozygous transgenic lines. A minimum of 12 antisense lines were generated for both GF14 ε and GF14 μ.

Plant Growth.

*Arabidopsis* plants were grown in constant light at 22° C. on germination media plates oriented in a vertical position or in flats of Transplant mix A (Vergro, Tampa, Fla.). Starch degradation experiments were done by transferring the plants to dark and samples taken at three hour intervals.

Starch Analysis.

Starch was visualized by Lugol's iodine staining reagent (Sigma). Leaves from 10-day-old plants were harvested and blanched in 80% (vol/vol) ethanol. After rinsing with double-distilled water the leaves were stained with Lugol's reagent and briefly destained with water. Stained plants and leaves were photographed with an Olympus SZH10 stereo dissecting microscope and DP10 digital camera.

Enzymatic measurement of starch in leaves was performed by using a method adapted from Zeeman et al. (Zeeman et al., 1998). Rosettes were harvested and weighed, then boiled in 80% ethanol. After clearing, the samples were ground in a mortar and pestle in 80% ethanol and the crude starch pellet was recovered by centrifugation at 5,000 rpm for 5 min in a Beckman JA20 rotor and J2-21 centrifuge. The crude starch was resuspended in 80% ethanol and repelleted two more times. The final pellet was dried and resuspended in double-distilled water, then placed at 85° C. for 10 min. The starch solution was then digested with 3 mg/ml amyloglucosidase and 20 units of amylase in 20 mM calcium acetate pH 4.5 buffer for 24 h at 37° C. The final concentration of liberated glucose was determined by using a glucose oxidase assay kit (Sigma).

Purified starch granules used for immunological and biochemical studies were extracted from plants by using the Mops-based protocol reported by Zeeman et al. (1998). Essentially, whole plants minus the roots were ground in a Mops buffer system, washed with SDS-containing buffer, and finally washed extensively with deionized water. Yields were calculated on a milligrams of isolated starch per gram fresh plant weight basis.

Relative amylose/amylopectin ratios from purified starch granules were assayed by using iodine starch spectral analysis as described by Konishi et al. (1985).

Immunolocalization and Blotting.

Transmission electron microscopy using GF14 isoform-specific polyclonal primary antibodies and gold secondary antibodies was used to localize 14-3-3 proteins in the starch granules of *Arabidopsis* leaves by the method previously described (Bihn et al., 1997). Starch granules for immunoblotting were first treated with thermolysin to ensure removal of surface-associated proteins as described by Mu-Foster et al. (1996), and intrinsic starch granule proteins were separated by SDS/PAGE and transferred to nitrocellulose membranes as described (Sehnke et al., 2000).

14-3-3 Protein-Binding Motif Analysis of Starch Granule-Associated Proteins.

A BLAST search (Altschul et al., 1997) for the 14-3-3 phosphoserine/threonine-binding consensus motif (RXXS/TXP) was conducted on the available plant starch-associated protein sequences by using the National Institutes of Health BLAST web server.

Immunocapture Experiments.

Commercial corn starch (Argo, Englewood Cliffs, N.J.) was used as a source of protein complexes for the immunocapture experiments. The starch was first digested with thermolysin to remove surface-associated proteins (Mu-Forster et al., 1996), then washed and digested at 25° C. with α-amylase and amyloglucosidase in 100 mM Tris-acetate buffer, pH 7.5, containing 100 mM KCl, 2.5 mM DTT, 10% (vol/vol) glycerol, 25 mM NaF, 3 mM $CaCl_2$, and 0.1% BSA for 3 h by using a protocol adapted from MacDonald and Preiss (MacDonald et al., 1983). Undigested material was removed by ultracentrifugation in a Beckman SW55 Ti rotor at 4° C. at 50,000 rpm for 30 min. Supernatant was transferred to a plastic conical tube and BSA was added to a final concentration of 0.1%. The supernatant was passed over anti-14-3-3 ε- and μ-conjugated Sepharose made from CNBr-activated Sepharose (Amersham Pharmacia Biotech) and the 14-3-3 protein antisera IgG fractions (Sehnke et al., 2000). A control column containing antibodies raised against the transcriptional cofactor GIP1 (unpublished data) was used as a negative control. The columns were loaded with the starch-derived protein extract, then washed three times with phosphate-buffered saline (PBS), pH 7.6, containing 25 mM NaF. The processed beads were boiled for 1 min in 2×SDS/PAGE sample buffer. The beads were removed by centrifugation and supernatant was loaded onto 10% polyacrylamide gels before SDS/PAGE. The proteins were transferred to nitrocellulose and blocked overnight with Blotto Tween (Harlow et al., 1988). The membranes were probed with antiserum to the *Zea mays* (Zm)SSIII DU1 (Cao et al., 1999). The membrane was washed and incubated with horseradish peroxidase-conjugated antibodies to rabbit IgG. Labeled bands were identified by the process of chemiluminescence, using SuperSignal West Pico Chemiluminescent Substrate according to the supplier's instructions (Pierce).

Biotinylated 14-3-3 Protein Overlay Experiments.

To identify corn starch proteins that are potential targets for 14-3-3 protein binding, proteins from corn starch were separated by electrophoresis and assayed by using a blot overlay procedure with biotinylated recombinant 14-3-3 Zm GF14-12. Zm GF14-12 was expressed in *E. coli* and purified by nickel-Sepharose chromatography as described previously (de Vetten et al., 1994). The protein was dialyzed against 100 mM sodium borate, pH 8.8, overnight before addition of biotinamidocaproate N-hydroxysuccinimide ester in DMSO at a ratio of 50 μg of ester per mg of protein. After 4 h at room temperature, the reaction was terminated by the addition of 1 M ammonium chloride, pH 8.0. The biotinylated 14-3-3 protein was dialyzed exhaustively against PBS over the course of 2 days at 4° C. Proteins from 10 mg of corn starch boiled in SDS/PAGE sample buffer were separated by PAGE and transferred to nitrocellulose, then incubated overnight at 4° C. with biotinylated 14-3-3 protein in PBS containing 1% BSA. The blot was washed three times with PBS/1% BSA and incubated for 30 min with streptavidin-conjugated horseradish peroxidase diluted in PBS/1% BSA. The blot was washed three additional times and the 14-3-3-bound protein was identified by using chemiluminescence as described above.

EXAMPLE 1

Transgenic *Arabidoysis* Plants Expressing Antisense cDNA

Transgenic *Arabidopsis* plants expressing antisense cDNA of At 14-3-3s GF14 ε and μ, two members of the ε subgroup of 14-3-3 proteins, displayed normal growth behavior but demonstrated phenotypic changes relative to wild-type plants with regard to starch accumulation in leaves. Although the absolute level of starch present in the leaves of *Arabidopsis* depended upon culture conditions and the lines examined, the leaves of plants from all 12 GF14 ε and GF14 μ antisense lines consistently accumulated increased starch levels relative to leaves of wild-type plants. Iodine staining indicated that the increased starch accumulation was equally distributed throughout the leaves of the antisense plants (FIGS. 1A–C). Quantitative measurements of the starch present in the leaves of plants grown in constant light revealed an approximately 2-fold increase in total starch content in antisense plants over wild-type plants (28±7 mg of starch per g fresh weight in transgenic plants vs. 15±3 mg of starch per g fresh weight in wild-type plants). The extractable starch from antisense plants was approximately 4-fold higher than that from wild-type plants (43±5 mg of starch per g fresh weight vs. 9±2 mg of starch per g fresh weight, respectively). Isolated starch granules from antisense plants were used to evaluate the absorption spectra of the iodine/starch complex, as an indicator of unbranched and branched glucan ratios. The absorption spectrum of the iodine/starch complex from antisense plants (FIG. 2, spectrum B) was blue-shifted relative to the absorption spectrum of the iodine/starch complex from wild-type plants (FIG. 2, spectrum A), suggesting that the starch from antisense plants has an increase in branched glucan content. This premise is further supported by the observation that the percentage of gelatinizable starch from antisense plants was reduced relative to that found in wild-type plants (data not shown).

To determine whether altered degradation rates might be responsible for the elevated starch accumulation in 14-3-3 antisense plants, plants were grown in constant light and harvested after a dark period of 18 h. Iodine staining of leaves at the end of the dark period was indistinguishable between wild-type (FIG. ID) and antisense plants (FIG. 1E and 1F). To measure the rate of starch breakdown, leaf samples were taken every 3 h after the plants were placed in the dark. Wild-type plants degraded starch at a rate of approximately 1 mg of starch per g fresh weight per h, whereas the antisense plants cleared starch from their leaves at rates of approximately 1.3 to 1.5 mg of starch per g fresh weight per h. This result indicates that the starch degradation pathway is fully functional in the antisense plants and suggests that reduced negative regulation of starch biosynthesis is responsible for increased starch in the 14-3-3 antisense plants. The 14-3-3 proteins would therefore appear to function as inhibitory proteins in starch metabolism by normally shutting down starch biosynthesis, thereby playing a key regulatory role in carbon allocation that is similar to their role in nitrogen fixation.

EXAMPLE 2

Immunolocalization of 14-3-3 Proteins in Starch Granules

Antibodies to 14-3-3 proteins were used in an immunolocalization electron microscopy experiment looking at starch granules in the leaves of wild-type *Arabidopsis*. The inside of chloroplast starch granules was densely decorated by antibodies that recognize eight non-ε subgroup members (FIG. 3B). Antibodies specific to GF14 ε also decorated the inside of starch granules, but more sparsely (FIG. 3C). This limited amount of 8 in the starch granules of wild-type plants may explain why the antisense plants displayed reduced levels of starch-associated GF 14 ϵ, whereas the cytoplasmic levels of ϵ remained reasonably normal (data not shown). These data also indicate that non-ϵ 14-3-3 proteins may be involved in starch biosynthesis, although no phenotypic data yet exist to support this conclusion. The relationship among the 14-3-3 isoforms present in starch grains, as well as the question of whether active forms of 14-3-3 proteins exist as homodimers or heterodimers, is not well established and therefore will need to be addressed in future studies.

EXAMPLE 3
Western Blot Analysis of Reduction in 14-3-3 Protein in Plants

Figure 4:
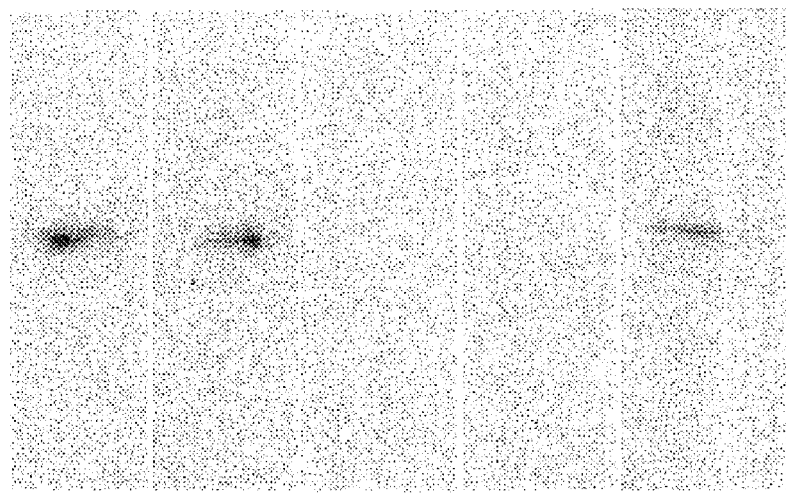
FIG. 4 shows reduction of GF14 ε and μ protein levels in the starch granules of antisense plants and presence of 14-3-3 proteins in commercial corn starch. Isolated starch granules from wild-type and antisense *Arabidopsis* were treated with thermolysin to remove externally attached proteins and subjected to SDS/PAGE Western analysis with 14-3-3 protein antibodies (Mu-Forster et al., 1998). Protein extracts from 3 mg of starch from wild-type (lanes 1 and 2), GF14 ε antisense (lane 3), and GF14 μ antisense (lane4) plants were probed with antibodies recognizing GF14 ε (lanes 1 and 3) and μ (lanes 2 and 4). A clear reduction of these 14-3-3 isoforms is observed in the starch-granule proteins of antisense plants. A 3-mg sample of commercial corn starch was processed as described above and the blot was probed with antibodies that recognize maize 14-3-3 proteins (lane 5), indicating the presence of 14-3-3 proteins in starch grains from maize.

To confirm that 14-3-3 proteins are present within chloroplast starch granules and that increased starch production is a result of decreased 14-3-3 proteins, starch granules from wild-type, GF14 ϵ, and GF14 μ antisense plant leaves were biochemically analyzed for the presence of 14-3-3 proteins. Purified starch granules were incubated with the protease thermolysin to remove external proteins, washed, boiled in SDS/PAGE sample buffer, and analyzed on SDS/PAGE by Western analysis with antibodies specific to 14-3-3 proteins GF14 ϵ or μ (Sehnke et al., 2000). Wild-type starch contained both GF14 ϵ and μ (FIG. 4 lanes 1 and 2), whereas antisense starch did not contain detectable amounts of either (FIG. 4 lanes 3 and 4). This coregulated suppression is not surprising, as the identity between cDNAs is approximately 70% and therefore both mRNAs are reduced by antisense regulation in planta. Western analysis of whole-leaf extracts did not demonstrate a pronounced decrease in GF14 ϵ and μ proteins (data not shown). Starch granule-specific reduction of GF14 ϵ and μ may be reflective of a selection process for chloroplastid 14-3-3 proteins, perhaps pressured by an as-yet-uncharacterized import mechanism (Sehnke et al, 2000). The presence of ϵ and μ 14-3-3 proteins in starch granules is significant in that they appear essential for proper regulation of leaf starch biosynthesis in *Arabidopsis*. In addition, commercial starch from maize also possesses 14-3-3 proteins (FIG. 4 lane 5), suggesting that 14-3-3 protein regulation of starch synthesis is used by crops and occurs in other plastids, such as amyloplasts, and is not limited to photosynthetically active plastids.

EXAMPLE 4
Consensus 14-3-3-binding Motif in SSIII Coding Sequences

Figures 5, 6:
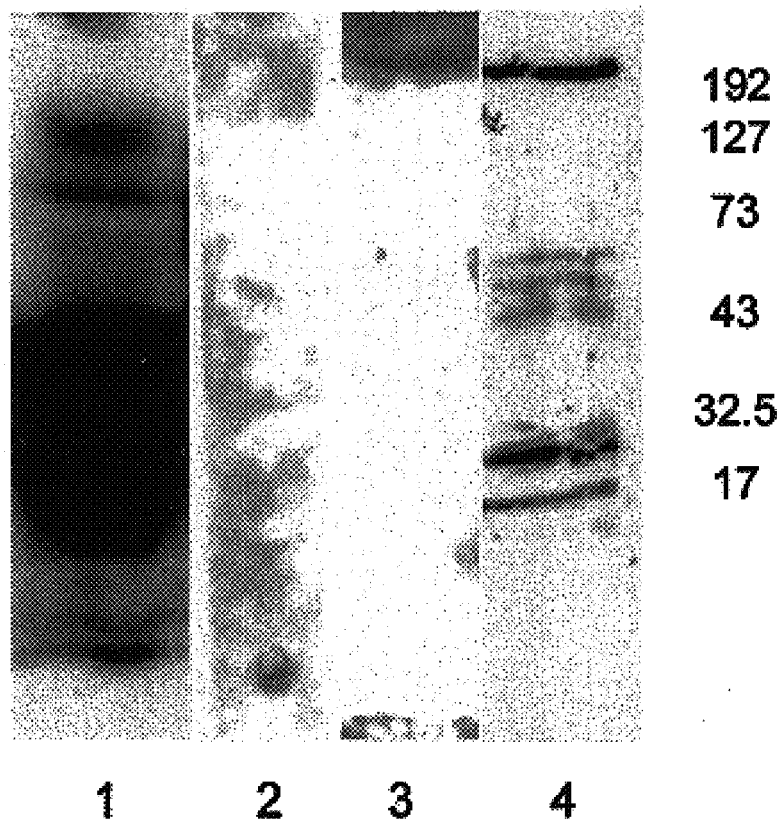
FIG. 5 shows consensus 14-3-3-binding sites in SSII coding sequences. The phosphoserine/threonine-containing binding sequence for 14-3-3 proteins is present in all known members of the SSIII family listed in GenBank: SSIII from *Vigna unguiculata* (Vigna SSIII AJ225088), SSIII from *Solanum tuberosum* (Potato SSIII X94400 and X95759), SSIII DU1 from *Zea mays* (Dull1 SS, AF023159), SSIII from *Triticum aestivum* (Triticum SSIII, AF258608), SSIII from *Aegilops tauschii* (Aegilops SSIII, AF258609), and a predicted SSIII from *Arabidopsis thaliana* (At SSIII, AL021713). The 14-3-3 protein consensus binding domain (BD) and the NR 14-3-3 binding domain are shown for comparison.
FIG. 6 shows binding of 14-3-3 proteins to DU1 or DU1-like SS. Proteins isolated from digested starch were passed over an anti-14-3-3 column and a control column. Bound proteins were eluted, separated by electrophoresis, transferred to nitrocellulose, and probed with antiserum to ZmSSIII DU1. The anti-GF14 column retained the DU1 cross-reactive protein (largely degraded from multiple processing steps) (lane 1), whereas the negative control column did not (lane 2). Proteins extracted directly from gelled starch were separated by electrophoresis and transferred to nitrocellulose. Probing with biotinylated Zm GF14-12 identified a 14-3-3-binding protein of approximately 200 kDa (lane 3). Probing with antiserum to ZmSSIII DU1 labeled proteins of a similar size (lane 4).

Although a chloroplast-localized 14-3-3 protein partner in starch synthesis has not been reported, a search of all available starch-related enzyme sequences for the consensus 14-3-3-binding motif revealed the SSII family as an obvious potential target within the plastid (FIG. 5). SSIII members from potato, *Arabidopsis, Vigna unguiculata, Aegilops tauschii, Triticum aestivum*, and maize all contain a conserved hexapeptide motif very similar to the 14-3-3 protein binding site of NR. This is the only example of an entire family sharing such a highly conserved potential binding site among the plastid enzyme sequences currently available. It is interesting to note that SSIII is directly involved in the production of amylopectin and has significant control over other SS isoforms (Edwards et al. 1999), perhaps explaining both starch accumulation and the qualitative shift in branched glucan content observed in 14-3-3 antisense plants.

Immunocapture experiments with anti-GF14 column and proteins isolated from processed corn starch were used to experimentally determine whether starch granule 14-3-3 proteins associate directly with SSIIIs. Commercial corn starch was chosen as a source of proteins because of its bulk availability and antibodies to the maize SSIII enzyme were available (Cao et al., 1999). SDS/PAGE and Western analysis of immunocaptured proteins identified ZmSSIII DU1 as a starch 14-3-3 partner protein (FIG. 6). The molecular masses of the captured protein bands were lower than the mass of intact ZmSSIII DU1 (see below); however, this can be attributed to breakdown of SSIII DU1 during the starch degradation process (Cao et al., 1999). Although ZmSSIII DU1 was reported as primarily located in the soluble fractions of kernel extracts, low levels of ZmSSIII DU1 in starch were observed in starch granules (Cao et al., 1999). To confirm that SSIII DU1 is present inside the corn starch grains, and to avoid the degradation observed in the immunocapture experiment, protease-treated commercial starch was boiled in SDS/PAGE sample buffer, separated by electrophoresis, and transferred to nitrocellulose. The blot was then probed with biotinylated recombinant 14-3-3 protein, and bound bands were detected by chemiluminescence (FIG. 6, lane 3). Biotinylated 14-3-3 protein bound to a protein of approximately 200 kDa, whose migration corresponds to a main band recognized by ZmSSIII DU1 antibodies (FIG. 6, lane 4). These data provide correlative support for an interaction between 14-3-3 proteins and DU1 or DU1-like proteins within starch grains, but confirmation of the interaction awaits detailed characterization of the protein complex.

The biological significance of choroplastid 14-3-3 proteins, specifically the ϵ subgroup, in starch metabolism is clearly demonstrated through the use of 14-3-3 antisense plants of the present invention. Additionally, the increase in branched glucans vs. nonbranched glucans in the antisense plants would seem contrary to simply increasing the cytosolic flux of starch precursors, as would be the effect of altered upstream regulation of starch metabolism. Further experiments are necessary to confirm the interaction between 14-3-3 proteins and SSIIIs or other enzymes regulated in this pathway, and the possibility of other plastid enzymes being regulated by 14-3-3 proteins is not excluded. However, the specific localization of the 14-3-3 proteins in the starch granules should, in this instance, serve to limit the range of possible 14-3-3 protein targets to those enzymes located within starch-producing plastids.

These results show that starch composition and accumulation can be directly regulated by plastid 14-3-3 proteins. The data presented herein are consistent with a mechanism whereby starch production in continuously illuminated plants is limited through inactivation of SSs by phosphorylation and 14-3-3 protein binding. Without 14-3-3 proteins to complete the inactivation step, starch continues to accumulate beyond normal levels.

It should be understood that the examples and embodiments described herein are for illustrative purposes only and that various modifications or changes in light thereof will be suggested to persons skilled in the art and are to be included within the spirit and purview of this application and the scope of the appended claims.

References

U.S. Pat. No. 5,365,016
U.S. Pat. No. 5,498,831
U.S. Pat. No. 5,789,657
U.S. Pat. No. 5,792,920
U.S. Pat. No. 5,824,798
U.S. Pat. No. 5,830,724
U.S. Pat. No. 5,856,467
U.S. Pat. No. 5,959,180
U.S. Pat. No. 5,962,769
U.S. Pat. No. 5,981,852

U.S. Pat. No. 5,998,701

U.S. Pat. No. 6,013,861

Altschul, S. F., T. L. Madden, A. A. Schaffer, J. Zhang, Z. Zhang, W. Miller, and D. J. Lipman (1997) *Nucleic Acids Res.* 25:3389–3402.

Bachmann, M., J. L. Huber, P. C. Liao, D. A. Gage, and S. C. Huber (1996) *FEBS Lett.* 387:127–131.

Bechtold, N. and G. Pelletier (1998) *Methods Mol. Biol.* 82:259–266.

Bihn, E. A., A. L. Paul, S. W. Wang, G. W. Erdos, and R. J. Ferl (1997) *Plant J.* 12:1439–1445.

Cao, H., J. Imparl-Radosevich, H. Guan, P. L. Keeling, M. G. James, and A. M. Myers (1999) *Plant Physiol.* 120:205–215.

Carrer, H., P. Maliga (1995) "Targeted insertion of foreign genes into the tobacco plastid genium without physical linkage to the selectable marker" *Biotechnology* 13:791–794.

Chung, H. J., P. C. Sehnke, and R. J. Ferl (1999) *Trends Plant Sci.* 4:367–371.

Craig, J., J. R. Lloyd, K. Tomlinson, L. Barber, A. Edwards, T. L. Wang, C. Martin, C. L. Hedley, and A. M. Smith (1998) *Plant Cell* 10:413–426.

Daugherty, C. J., M. F. Rooney, P. W. Miller, and R. J. Ferl (1996) *Plant Cell* 8:1239–1248.

de Vetten, N. C. and R. J. Ferl (1994) *Plant Physiol.* 106:1593–1604.

Edwards, A., D. C. Fulton, C. M. Hylton, S. A. Jobling, M. Gidley, U. Rossner, C. Martin, and A. M. Smith (1999) *Plant J.* 17:251–261.

Harlow, E. and D. Lane (1988) *Antibodies: A Laboratory Manual* (Cold Spring Harbor Lab. Press, Plainview, N.Y.).

Holsters, M., D. de Waele, A. Depicker, E. Messens, M. van Montagu, and J. Schell (1978) *Mol. Gen. Genet.* 163:181–187.

Imparl-Radosevich, J. M., D. J. Nichols, P. Li, A. L. McKean, P. L. Keeling, and H. Guan (1999) *Arch. Biochem. Biophys.* 362:131–138.

Konishi, Y., H. Mojima, K. Okuno, M. Asaoka, and H. Fuwa (1985) *Agric. Biol. Chem.* 49:1965–1971.

Krysan, P. J. (1996) "Identification of transferred DNA insertions with *Arabidopsis* genes involved in signal transduction and ion transport" Proc. *Natl. Acad. Sci. USA* 93:8145–8150.

Lloyd, J. R., V. Landschutze, and J. Kossmann (1999) *Biochem. J.* 338:515–521.

MacDonald, F. D. and J. Preiss (1983) *Plant Physiol.* 73:175–178.

Moorhead, G., P. Douglas, N. Morrice, M. Scarabel, A. Aitken, and C. MacKintosh (1996) *Curr. Biol.* 6:1104–1113.

Moorhead, G., P. Douglas, V. Cotelle, J. Harthill, N. Morrice, S. Meek, U. Deiting, M. Stitt, M. Scarabel, A. Aitken, and C. MacKintosh (1999) *Plant J.* 18:1–12.

Mu-Forster, C., R. Huang, J. R. Powers, R. W. Harriman, M. Knight, G. W. Singletary, P. L. Keeling, and B. P. Wasserman (1996) *Plant Physiol.* 111:821–829.

Mu-Forster, C. and B. P. Wasserman (1998) *Plant Physiol.* 116:1563–1571.

Preiss, J. and M. N. Sivak (1998) *Genet. Eng.* 20:177–223.

Sehnke, P. C. and R. J. Ferl (1996) *Curr. Biol.* 6:1403–1405.

Sehnke, P. C., R. Henry, K. Cline, and R. J. Ferl (2000) *Plant Physiol.* 122:235–242.

Smith, A. M. (1999) *Curr. Opin. Plant Biol.* 2:223–229.

Sokolov, L. N., A. Dejardin, and L. A. Kleczkowski (1998) *Biochem. J.* 336:681–687.

Sun, J., T. W. Okita, and G. E. Edwards (1999) *Plant Physiol.* 119:267–276.

Toroser, D., G. S. Athwal, and S. C. Huber (1998) *FEBS Lett.* 435:110–114.

Wu, K., M. R. Rooney, and R. J. Ferl (1997) *Plant Physiol.* 114:1421–1431.

Zeeman, S. C., F. Northrop, A. M. Smith, and T. Rees (1998) *Plant J.* 15:357–365.

---

We claim:

1. A method for enhancing starch production in a plant, said method comprising inhibiting the expression of a 14-3-3 protein of said plant, wherein expression of said 14-3-3 protein is inhibited by expressing a heterologous polynucleotide in said plant that comprises a nucleotide sequence that is antisense to
   (i) the coding region of the nucleotide sequence shown in SEQ ID NO. 1 that encodes an Epsilon isoform of 14-3-3 protein having the amino acid sequence shown in SEQ ID NO. 2; or
   (ii) the coding region of the nucleotide sequence shown in SEQ ID NO. 3 that encodes a Mu isoform of 14-3-3 protein having the amino acid sequence shown in SEQ ID NO. 4.

2. The method according to claim 1, wherein said plant is a monocot.

3. The method according to claim 2, wherein said monocot is selected from the group consisting of maize, wheat, barley, rice, and oats.

4. The method according to claim 1, wherein said plant is a dicot.

5. The method according to claim 4, wherein said dicot is selected from the group consisting of tobacco, potato, cabbage, soybeans, and sweet potato.

6. The method according to claim 1, wherein said plant is *Arabidopsis*.

7. A method for preparing a plant that exhibits enhanced starch production, said method comprising introducing into said plant a heterologous polynucleotide that comprises a nucleotide sequence that is antisense to
   (i) the coding region of the nucleotide sequence shown in SEQ ID NO. 1 that encodes an Epsilon isoform of 14-3-3 protein having the amino acid sequence shown in SEQ ID NO. 2; or
   (ii) the coding region of the nucleotide sequence shown in SEQ ID NO. 3 that encodes a Mu isoform of 14-3-3 protein having the amino acid sequence shown in SEQ ID NO. 4, wherein expression of said 14-3-3 protein is inhibited by expressing said polynucleotide in said plant.

8. The method according to claim 7, wherein said plant is a monocot.

9. The method according to claim 8, wherein said monocot is selected from the group consisting of maize, wheat, barley, rice, and oats.

10. The method according to claim 7, wherein said plant is a dicot.

11. The method according to claim 10, wherein said dicot is selected from the group consisting of tobacco, potato, cabbage, soybeans, and sweet potato.

12. The method according to claim 7, whrerin said plant is *Arabidopsis*.

13. A plant or plant material that comprises a heterologous polynucleotide that comprises a nucleotide sequence that is antisense to
   (i) the coding region of the nucleotide sequence shown in SEQ ID NO. 1 that encodes an Epsilon isoform of 14-3-3 protein having the amino acid sequence shown in SEQ ID NO. 2; or
   (ii) the coding region of the nucleotide sequence shown in SEQ ID NO. 3 that encodes a Mu isoform of 14-3-3 protein having the amino acid sequence shown in SEQ ID NO. 4.

14. The plant or plant material according to claim 13, wherein said plant is a monocot or said plant material is from a monocot plant.

15. The plant or plant material according to claim 14, wherein said monocot is selected from the group consisting of maize, wheat, barley, rice, and oats.

16. The plant or plant material according to claim 13, wherein said plant is a dicot or said plant material is from a dicot plant.

17. The plant or plant material according to claim 16, wherein said dicot is selected from the group consisting of tobacco, potato, cabbage, soybeans, and sweet potato.

18. The plant or plant material according to claim 13, wherein said plant or plant material is produced according to the method of claim 7.

19. The plant or plant material according to claim 13, wherein said plant material is selected from the group consisting of plant tissue, plant cells, plant seeds, and protoplasts.

20. The plant or plant material according to claim 13, wherein said plant is *Arabidopsis*.

* * * * *

UNITED STATES PATENT AND TRADEMARK OFFICE
CERTIFICATE OF CORRECTION

PATENT NO. : 6,867,350 B2
DATED : March 15, 2005
INVENTOR(S) : Robert J. Ferl et al.

It is certified that error appears in the above-identified patent and that said Letters Patent is hereby corrected as shown below:

Column 2,
Line 65, "ϵ and (Fig. 1B)" should read -- ϵ (Fig. 1B) --.

Column 3,
Line 41, "SSII" should read -- SSIII --.

Column 4,
Line 47, "in plants" should read -- *in planta* --.

Column 8,
Line 66, "of 8" should read -- of ϵ --.

Column 9,
Line 48, "SSII" should read -- SSIII --.

Signed and Sealed this

Twelfth Day of July, 2005

JON W. DUDAS
*Director of the United States Patent and Trademark Office*